United States Patent

Marques

[11] Patent Number: 5,506,301
[45] Date of Patent: Apr. 9, 1996

[54] TREATMENT OF ISOCYANATE RESIDUE

[75] Inventor: Federico T. Marques, Baytown, Tex.

[73] Assignee: Bayer Corporation, Pittsburgh, Pa.

[21] Appl. No.: 166,137

[22] Filed: Dec. 13, 1993

[51] Int. Cl.⁶ .............................. C08K 3/20; C08L 75/00
[52] U.S. Cl. .................... 524/591; 524/590; 524/284; 588/205; 588/206; 588/251
[58] Field of Search .................... 521/49; 524/590, 524/591, 284; 588/205, 206, 251

[56] References Cited

U.S. PATENT DOCUMENTS

| | | | |
|---|---|---|---|
| 3,084,182 | 4/1963 | McElroy | 260/471 |
| 3,128,310 | 4/1964 | Koch | 260/582 |
| 3,180,852 | 4/1965 | Pfirschke | 260/77.5 |
| 3,210,395 | 10/1965 | McDougall | 260/453 |
| 3,331,876 | 7/1967 | Van Horn et al. | 260/582 |
| 3,755,215 | 8/1973 | Khoury et al. | 260/2.5 AT |
| 4,032,574 | 6/1977 | Keshi et al. | 260/570 D |
| 4,091,009 | 5/1978 | Cassata | 260/453 PH |
| 4,105,686 | 8/1978 | Raes et al. | 260/453 PH |
| 4,137,266 | 1/1979 | Cassata | 260/578 |
| 4,251,401 | 2/1981 | Reischl | 260/9 |
| 4,297,456 | 10/1981 | Reischl et al. | 525/452 |
| 4,311,800 | 1/1982 | Reischl | 521/109 |
| 4,788,329 | 11/1988 | Nummy | 560/330 |

Primary Examiner—Paul J. Thibodeau
Assistant Examiner—Mary Critharis
Attorney, Agent, or Firm—Joseph C. Gil; Richard E. L. Henderson

[57] ABSTRACT

The present invention is directed to a process for treating an isocyanate distillation residue comprising (a) mixing acidified water with an organic material selected from limonene, limonene oxide, menthoxyacetic acid, menthyl chloroformate, and γ-terpinene to form a first mixture;

(b) mixing an isocyanate distillation residue with the mixture of step (a) to form a second mixture; and (c) stirring the mixture of step (b) until the pH of the mixture is about 7.

1 Claim, No Drawings

TREATMENT OF ISOCYANATE RESIDUE

BACKGROUND OF THE INVENTION

The present invention relates to the treatment of isocyanate residues. It is well known to prepare isocyanates by reacting the corresponding amine with phosgene in an organic solvent following phosgenation, the resulting isocyanate is generally vacuum distilled to improve the purity of the resultant product. This distillation procedure produces an undistillable residue. The chemical composition of the residue is not clear, and the residue itself poses a disposal problem. The prior art is replete with attempts to utilize and/or treat the above-mentioned isocyanate residue. Typical of such treatments are reaction with aromatic phenols (U.S. Pat. No. 3,084,182), hydrolysis (U.S. Pat. Nos. 3,128,310, 3,331,876, 4,091,009, 4,137,266, and 4,311,800), ammonolysis (U.S. Pat. No. 3,210,395), reaction with various active-hydrogen containing materials (U.S. Pat. Nos. 3,180,852, 3,755,215, and 4,032,574), and grinding the residue and thereafter suspending the resultant ground material (U.S. Pat. Nos. 4,251,401 and 4,297,456). To date, none of these techniques have alleviated the problem of the waste management of the isocyanate residues.

The present invention is directed to the discovery of a relatively simple technique for treating isocyanate distillation residues. The treatment results in a yellow solid powder and an aqueous liquid phase that for distillation residues of many isocyanates is nearly colorless or lightly colored. The liquid phase can be easily treated as waste water, whereas the solid powder can be readily used as a filler material for polyurethane-based resins and foams.

SUMMARY OF THE INVENTION

More particularly, the present invention is directed to a process for treating an isocyanate distillation residue comprising (a) mixing acidified water with an organic material selected from the group consisting of

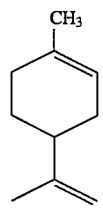

(I)

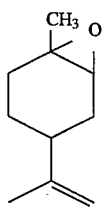

(II)

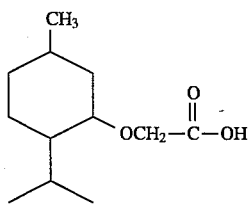

(III)

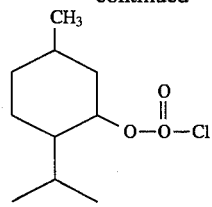

(IV)

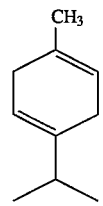

(V)

to form a first mixture;

(b) mixing an isocyanate distillation residue with the mixture of step (a) to form a second mixture; and (c) stirring the mixture of step (b) until the pH of the mixture is about 7.

DETAILED DESCRIPTION OF THE INVENTION

As used herein, the phrase, "isocyanate distillation residue", means the distillation residue remaining after removal of substantially all the monomeric isocyanate from the crude isocyanate reaction mixture resulting from the phosgenation of an organic amine. Such distillation residues are known in the art, and are described for example in U.S. Pat. Nos. 3,084,182, 3,128,310, 3,331,876, 4,091,009, 4,137,266, 4,311,800, 3,180,852, 3,755,215, 4,032,574, 4,251,401, and 4,297,456, the disclosures of which are herein incorporated by reference. Preferred residues are those resulting from the production of toluene diisocyanate, hexamethylene diisocyanate, and 4,4'-methylenebis(cyclohexyl isocyanate).

The organic materials useful herein are those of the following formulas:

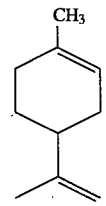

(I)

Limonene

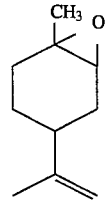

(II)

Limonene oxide

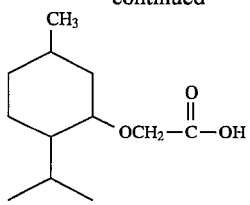

Menthoxyacetic acid

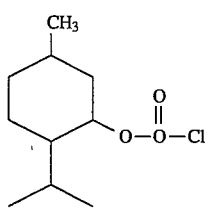

Menthyl chloroformate

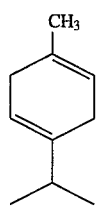

γ-Terpinene

The respective stereoisomers and mixtures thereof are, of course, also suitable.

The presently preferred material is limonene (or 1-methyl-4-(1-methylenyl)cyclohexene) (formula I above). Limonene is a known material and can be isolated from the ethereal oils of various natural plants including lemon, orange, caraway, dill, bergamot, and mandarin peel oil. See, for example, U.S. Pat. No. 4,788,329.

In the first step of the process, the organic material is mixed with acidified water in an amount of from 1 to 100 parts, preferably from 5 to 10 parts, per 100 parts by weight water. The water can be acidified by adding substantially any inorganic acid, such as hydrochloric acid, nitric acid, sulfuric acid, or the like. In general, the acidified water should have a pH of from 1 to 5, preferably from 1.5 to 3. Thereafter, the isocyanate residue is mixed with the water/organic material mixture in an amount of from 1 to 50 parts, preferably from 10 to 25 parts, per 100 parts by weight of water/organic mixture. The resultant mixture is then stirred until the hydrolysis is complete, which occurs when the pH of the mixture is about 7. The reaction occurs very smoothly and requires no heating. In fact, during the stirring, the reaction mixture should be maintained at a temperature below 40° C. (preferably between 20° and 30° C.), by cooling if necessary, in order to avoid particle clumping. In general, the reaction is complete after about 16 hours. Enhanced stirring, heating, and/or use of a catalyst (for example, a weak base such as an alkali metal carboxylate (e.g., sodium acetate) or a tertiary amine (e.g., triethylamine)) may speed the reaction time. Temperatures above 40° C. will accelerate the reaction and can cause clumping. Thus, it has been found that while heat can be used to accelerate the reaction, prolonged higher temperatures may cause clumping.

The time of reaction is also dependent upon the particular isocyanate residue used. Thus, for example, observed reaction times were (i) from 10 to 24 hours for residues resulting from the production of 4,4'-methylenebis(cyclohexyl isocyanate), (ii) from 10 to 36 hours for residues resulting from the production of hexamethylene diisocyanate, and (iii) from 2 to 6 hours for residues resulting from the production of toluene diisocyanate.

The various organic compounds tested for the process of the invention were the primary agents involved in the smooth hydrolysis. By themselves, however, the compounds (e.g., limonene) were only partially effective in forming the filterable product. However, with the addition of dispersants and/or surfactants (such as fatty acid esters or fatty amines, including coconut amines and blends thereof), the effectiveness was enhanced. One particularly preferred material was GOLDFLUSH II solvent degreaser, a commercially available product from Oil Center Research, Inc. This commercially available product contains about 92% by weight of limonene, with the balance being dispersants and surfactants. For purposes of this invention, the most preferred materials are blends containing about 90% by weight of a compound of one of the above formulas, with the balance being dispersant and/or surfactant containing coconut amines.

After the hydrolysis is complete, the remaining solids are filtered and dried. The solids can be washed and then rinsed with acetone or other solvent to remove any process water and/or contaminants. The solids are dried in a vacuum oven until moisture and/or solvent is removed. The solids can then be packaged and stored.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Examples 1–3

General procedure. To an open reaction vessel equipped with a stirrer was added 20 g of water, 0.1 g of 36% hydrochloric acid, and 1 g of GOLDFLUSH II solvent degreaser (about 92% limonene content; available commercially from Oil Center Research, Inc.). The mixture was stirred until milky (about 15 seconds). A 5 g sample of each isocyanate residue was heated to a temperature of about 40°–60° C. and then added slowly to the milky solution. The resultant mixture was stirred (with venting to allow for escape of carbon dioxide) for 8 to 10 hours or until hydrolysis was complete (as indicated by Fourier transform infrared spectroscopy and a solution pH of about 7 to 7.5). The solids that remained were removed by filtration and rinsed thoroughly with water and then with acetone to remove residual solvents. Moisture was removed from the solids in a vacuum oven. Suitable materials for further use as reactive isocyanates were those that were initially obtained as particulate solids that could be readily broken up into even finer particles.

Example 1

A distillation residue from the manufacture of hexamethylene diisocyanate by phosgenation formed very tiny droplets when dispersed. However, after 24 hours of constant mixing, these droplets formed a smooth paste that subsequently solidified into suitable particles.

Example 2

A blend of about 30–40% by weight of a distillation residue from the manufacture of hexamethylene diisocyanate and about 60–70% by weight of a distillation residue from the manufacture of 4,4'-methylenebis(cyclohexyl isocyanate) mixed readily and after 16 to 30 hours yielded suitable particles that were easily filtered and recovered.

Example 3

Concentrated distillation residues from the manufacture of toluene diisocyanate by phosgenation (containing about 40 to 70% toluene diisocyanate) tended to foam and solidify after 3 to 5 hours of mixing. The resultant solid from each such residue crumbled easily and was easily mixed. (It is sometimes necessary to add about 5 parts by weight of water to ensure uniform mixing of all the particles.) When uniform mixing is obtained, suitable particles were easily removed by filtration.

Example 4 (comparison)

Example 4 was a control experiment carried out according to Example 2 except for omitting the GOLDFLUSH II solvent degreaser. The initially obtained pasty brown liquid hardened to an unsuitable concrete-like solid.

Examples 5–19

Examples 5–11 were carried out according to Example 2 using the compounds according to the invention (see Table) instead of GOLDFLUSH II solvent degreaser. Each of these compounds yielded suitable isocyanate-containing particles that were easily filtered and recovered (although some samples were slightly sticky).

Table: Compounds used for Examples 5–11 according to the invention.

| Example | Component (a) |
| --- | --- |
| 5 | S-Limonene |
| 6 | R-Limonene |
| 7 | Racemic limonene |
| 8 | (+)-Limonene oxide |
| 9 | (−)-Menthoxyacetic acid |
| 10 | (−)-Menthyl chloroformate |
| 11 | γ-Terpinene |

Experiments carried out by the same method using allylbenzene, allylcyclopentane, racemic menthol, L-menthyl chloride, (−)-menthone, (+)-camphene, p-cymene, and α-terpineol produced unsuitable materials.

What is claimed is:

1. A process for treating an isocyanate distillation residue comprising (a) mixing water acidified to pH 1 to 5 using an inorganic acid with 1 to 100 parts by weight per 100 parts by weight of water of an organic material selected from the group consisting of

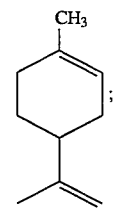

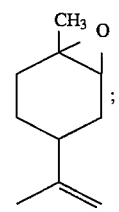

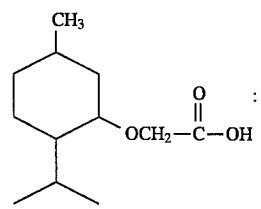

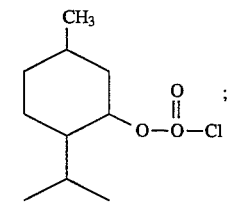

and

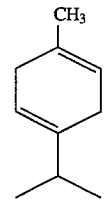

to form a first mixture;

(b) mixing 1 to 50 parts by weight of an isocyanate distillation residue per 100 parts by weight of the mixture of step (a) to form a second mixture; and (c) stirring the mixture of step (b) at a temperature below 40° C. until the pH of the mixture is about 7.

* * * * *